United States Patent
Yin et al.

(10) Patent No.: US 10,464,937 B2
(45) Date of Patent: Nov. 5, 2019

(54) PROCESS FOR PREPARING BETA-LACTAMASE INHIBITOR HYDROXYLUREA INTERMEDIATES

(71) Applicant: Merck Sharp & Dohme Corp., Rahway, NJ (US)

(72) Inventors: Jianguo Yin, Plainsboro, NJ (US); Zhijian Liu, Kendall Park, NJ (US); Nobuyoshi Yasuda, Mountainside, NJ (US); Mark Weisel, Stewartsville, NJ (US)

(73) Assignee: Merck Sharp & Dohme Corp., Rahway, NY (US)

( * ) Notice: Subject to any disclaimer, the term of this patent is extended or adjusted under 35 U.S.C. 154(b) by 0 days.

(21) Appl. No.: 16/334,054

(22) PCT Filed: Sep. 14, 2017

(86) PCT No.: PCT/US2017/051440
§ 371 (c)(1),
(2) Date: Mar. 18, 2019

(87) PCT Pub. No.: WO2018/053057
PCT Pub. Date: Mar. 22, 2018

(65) Prior Publication Data
US 2019/0233421 A1      Aug. 1, 2019

Related U.S. Application Data

(60) Provisional application No. 62/396,335, filed on Sep. 19, 2016.

(51) Int. Cl.
C07D 471/08 (2006.01)
C07F 7/08 (2006.01)

(52) U.S. Cl.
CPC .......... *C07D 471/08* (2013.01); *C07F 7/0892* (2013.01)

(58) Field of Classification Search
CPC .... C07D 471/08; C07D 491/08; C07F 7/0892
See application file for complete search history.

(56) References Cited

U.S. PATENT DOCUMENTS

2016/0024090 A1    1/2016  Seika
2016/0122350 A1*   5/2016  Miller .................. C07D 491/08
                                                                544/105
2016/0257684 A1    9/2016  Deshpande et al.

OTHER PUBLICATIONS

International Search Report and Written Opinion for PCT/US2017/051440, dated Nov. 7, 2017, 7 pages.
Compound Summary for CID 22623986, PubChem, 2007, 4, CID 22623986.

* cited by examiner

*Primary Examiner* — Jafar F Parsa
(74) *Attorney, Agent, or Firm* — Patricia A. Shatynski; John C. Todaro

(57) ABSTRACT

The present invention relates to processes for the preparation of N-protected (2S,5R)-6-hydroxy-7-oxo-N-piperidin-4-yl-1,6-diazabicyclo[3.2.1]octane-2-carboxamide intermediates. Such compounds have application in the preparation of beta-lactamase inhibitors such as 7-oxo-1,6-diazabicyclo[3.2.1]octane-2-carboxamides and esters, in particular, the beta lactamase inhibitor, (2S,5R)-7-oxo-N-piperidin-4-yl-6-(sulfoxy)-1,6-diazabicyclo[3.2.1]octane-2-carboxamide.

The present invention also encompasses intermediates useful in the disclosed processes and methods for their preparation.

14 Claims, No Drawings

PROCESS FOR PREPARING BETA-LACTAMASE INHIBITOR HYDROXYLUREA INTERMEDIATES

CROSS REFERENCE TO RELATED APPLICATIONS

This application is a U.S. National Phase application under 35 U.S.C. § 371 of PCT Application No. PCT/US2017/051440, filed Sep. 14, 2017 which claims priority under 35 U.S.C. § 119(e) from U.S. Provisional Application Ser. No. 62/396,335, filed on Sep. 19, 2016.

FIELD OF THE INVENTION

The present invention relates to processes for the preparation of N-protected (2S,5R)-6-hydroxy-7-oxo-N-piperidin-4-yl-1,6-diazabicyclo[3.2.1]octane-2-carboxamide hydroxylurea intermediates. Such compounds have application in the preparation of β-lactamase inhibitors such as 7-oxo-1,6-diazabicyclo[3.2.1]octane-2-carboxamides and esters, in particular, the β-lactamase inhibitor, (2S,5R)-7-oxo-N-piperidin-4-yl-6-(sulfoxy)-1,6-diazabicyclo[3.2.1]octane-2-carboxamide.

BACKGROUND OF THE INVENTION

Certain 7-oxo-1,6-diazabicyclo[3.2.1]octane-2-carboxamides are inhibitors of β-lactamase and, when used in conjunction with β-lactam antibiotics, can be effective for the treatment of bacterial infections, e.g., by overcoming resistance mechanisms. See, for example, International Patent Application Publication Nos. WO2009/091856 and WO2014/200786 which disclose 7-oxo-1,6-diazabicyclo[3.2.1]octane-2-carboxamides and their synthesis through a hydroxylurea intermediate. See also Mangion et al., 2011, *Org. Lett.* 13:5480-5483 and Miller et al., 2014, *Org. Lett.* 16:174-177.

U.S. Patent Application Publication No. US2003/0199541 discloses methods for preparing azabicyclic compounds which are useful as medicaments, in particular anti-bacterial agents. International Patent Application Publication No. WO2008/039420 discloses methods for preparing certain 7-oxo-2,6-diazabicyclo[3.2.0]heptane-2-carboxamides which are useful as β-lactamase inhibitors. International Patent Application Publication No. WO2010/126820 discloses the preparation of alkyl esters of N-protected oxo-azacycloalkylcarboxylic acids. These esters can be used as intermediates in the synthesis of 7-oxo-1,6-diazabicyclo[3.2.1]octane-2-carboxamides and esters. U.S. Patent Application Publication No. 2015/0141401 describes processes and intermediates useful for the synthesis of beta-lactamase inhibitors. Ji et al. (2012, *Tetrahedron* 68:1359) describe the acid-facilitated debenzylation of N-Boc, N-benzyl double protected 2-aminopyridinomethyl pyrrolidine derivatives.

SUMMARY OF THE INVENTION

The present invention relates to chemical processes and intermediates useful in the synthesis of a compound of Formula I, and related compounds, which are useful as intermediates in the preparation of compounds that are potent inhibitors of beta-lactamase.

The chemical processes of the present invention afford advantages over previously known procedures and include a more stable reaction product with fewer dimeric and polymeric impurities. In addition, the chemical processes of this invention improve the solubility of the reaction product reducing the need for class 2 solvents. See, e.g., Dwivedi, 2002, *Pharmaceutical Tech* 26:42-46.

Accordingly, the present invention provides a process for preparing a compound of Formula I:

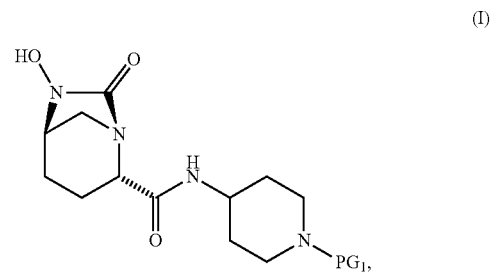

(I)

comprising
(A) reacting a compound of Formula II:

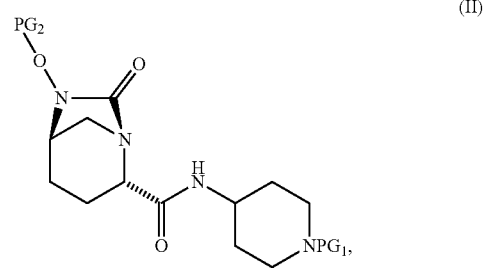

(II)

with a catalyst system and silylating reagent under hydrogenation conditions to obtain a compound of Formula III;

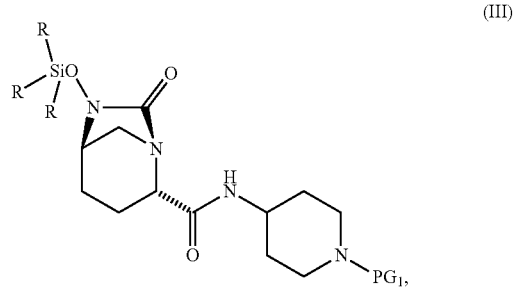

(III)

and
(B) hydrolyzing the compound of Formula III to form the compound of Formula I;
wherein each R group is independently a $C_{1-6}$ alkyl or phenyl.

In select embodiments, each instance of $PG_1$ is independently an amine protecting group which forms with the amino nitrogen to which it is attached a carbamate, a benzylamine, or a sulfonamide; and $PG_2$ is an oxygen protecting group (also referred to as an alcohol protecting group) selected from benzyl (Bn) or substituted benzyl, diphenylmethyl or substituted diphenylmethyl, and trityl or substituted trityl.

Compounds of Formula I are useful as intermediates that in combination with a series of additional steps results in a convergent synthesis of 7-oxo-1,6-diazabicyclo[3.2.1]octane-2-carboxamides and 2-carboxylic esters that can be used as β-lactamase inhibitors (BLIs).

Other embodiments, aspects and features of the present invention are either further described in or will be apparent from the ensuing description, examples, and appended claims.

DETAILED DESCRIPTION OF THE INVENTION

The present invention includes processes for preparing a compound of Formula I, and salts thereof, which involves in situ protection of the initially formed hydroxylurea during the reaction and subsequent isolation by deprotection and crystallization, as set forth above in the Summary of the Invention. These compounds and their salts are useful as intermediates for the preparation of certain beta-lactamase inhibitors.

The hydroxylurea of formula I is the penultimate intermediate in the synthesis of the beta-lactamase inhibitor, relebactam, and has previously been prepared by de-benzylation of intermediates of formula II using protecting groups such as CBz or Boc. A particular challenge with these reactions is the instability of the hydroxylurea product in solution, leading to formation of a number of dimeric and polymeric impurities. Additionally the low solubility of the product, required large volumes of a class 2 solvent (typically, THF) to retain solubility through catalyst filtration. Isolation after catalyst removal required lengthy removal times for this solvent leading to continued degradation. The processes of the invention provide benefits including increased stability of the reaction product and facile isolation of the intermediate.

Definitions

The amine protective group $PG_1$, as used in the reactions described herein, in combination with the amino nitrogen to which it is attached, can be a carbamate or a benzylamine or a sulfonamide. Suitable carbamate, benzylamine and sulfonamide protective groups and methods for their formation and cleavage are described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3$^{rd}$ edition, 1999, and 2$^{nd}$ edition, 1991. In one embodiment, $PG_1$ is (1) —C(=O)—O—$(CH_2)_{0-1}$—CH=$CH_2$, (2) —C(=O)—O—$CH_2$-AryB, wherein AryB is phenyl which is optionally substituted with from 1 to 3 substituents each of which is independently halo, —$NO_2$, —$C_{1-4}$ alkyl, or —O—$C_{1-4}$ alkyl, (3) —C(=O)—O—$C_{1-4}$ alkyl, or (4) —$CH_2$-AryC in which AryC is phenyl which is optionally substituted with from 1 to 3 substituents each of which is independently halo, —$NO_2$, —$C_{1-4}$ alkyl, or —O—$C_{1-4}$ alkyl. In another embodiment, $PG_1$ is t-butyloxycarbonyl (Boc), allyloxycarbonyl (Alloc), benzyloxycarbonyl (Cbz), p-methoxybenzyloxycarbonyl, p-nitrobenzyloxycarbonyl, p-bromobenzyloxycarbonyl, p-chlorobenzyloxycarbonyl, 2,4-dichlorobenzyloxycarbonyl, or benzyl. In still another embodiment, $PG_1$ is Boc. In still another embodiment, $PG_1$ is a sulfonyl group generated from sulfonyl halides such as methanesulfonyl chloride, chloromethanesulfonyl chloride, dichloromethanesulfonyl chloride, benzenesufonyl chloride, p-toluenesulfonyl chloride, p-fluorobenzenesulfonyl chloride, p-methoxybenzenesulfonyl chloride, 2-nitrobenzenesulfonyl chloride, 4-nitrobenzenesulfonyl chloride, 2,4-dichlorobenzenesulfonyl chloride, chloromethanesulfonyl chloride, p-trifluoromethylbenzenesulfonyl chloride and p-bromobenzenesulfonyl chloride. $PG_1$ is stable under conditions which the $PG_2$ group comes off.

$PG_2$ is an oxygen protective group. $PG_2$, in combination with the oxygen to which it is attached, is suitably benzyl (Bn) or substituted benzyl, diphenylmethyl or substituted diphenylmethyl, and trityl (triphenylmethyl, Tr) or substituted trityl. Suitable substitutions include $C_{1-4}$alkoxy, halogen, and nitro. An example of a substituted benzyl (or phenyl) is 4-methyl or 4-methoxy. In one embodiment, $PG_2$ is benzyl.

The term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl and pentyl alkyl isomers as well as n-, iso, sec- and t-butyl, n- and iso-propyl, ethyl and methyl. As another example, "$C_{1-4}$ alkyl" refers to any of n-, iso-, sec- and t-butyl, n- and isopropyl, ethyl and methyl. As another example, "$C_{1-3}$ alkyl" refers to any of n-propyl, isopropyl, ethyl and methyl.

The term "halogen" or "halo" means fluorine (F), chlorine (Cl), bromine (Br), and iodine (I). In specific embodiments, "halo" means chlorine or bromine. Similarly, "halo" means any of fluoro, chloro, bromo, and iodo groups. In specific embodiments, "halo" means chloro or bromo.

Unless expressly stated to the contrary, all ranges cited herein are inclusive. For example, a cycloalkyl ring described as a "$C_{3-8}$cycloalkyl" means the ring can contain 3, 4, 5, 6, 7 or 8 atoms in the ring. It is also to be understood that any range cited herein includes within its scope all of the sub-ranges as distinct embodiments within that range.

In addition, the term "or," as used herein, denotes alternatives that may, where appropriate, be combined; that is, the term "or" includes each listed alternative separately as well as their combination.

Unless expressly stated to the contrary, substitution by a named substituent is permitted on any atom provided such substitution is chemically allowed and results in a stable compound. A "stable" compound is a compound that can be prepared and isolated and whose structure and properties remain or can be caused to remain essentially unchanged for a period of time sufficient to allow use of the compound for the purposes described.

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

The compounds prepared via the present invention may be chiral as a result of asymmetric centers, chiral axes, or chiral planes as described in: E. L. Eliel and S. H. Wilen, *Stereochemistry of Carbon Compounds*, John Wiley & Sons, New York, 1994, pages 1119-1190), and may occur as single optical isomers or as mixtures of any number of the possible optical isomers, including racemates, racemic mixtures, diastereomers, diastereomeric mixtures, enantiomers, and enantiomeric mixtures. In certain instances, the compounds disclosed may exist as tautomers and all tautomeric forms are intended to be encompassed by the scope of the invention, even though only one tautomeric structure is depicted. That is, for the purposes of the present invention, a reference to a compound of Formula I is a reference to the compound per se, or to any one of its tautomers per se, or to mixtures of two or more tautomers.

Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Processes of the Invention

The processes of the invention, in certain embodiments, involve the in situ silyl protection of hydroxylurea to form the compound of formula III and isolation of the compound of formula I by reactive crystallization.

A compound of Formula II can be prepared as described in, for example, International Patent Application Publication Nos. WO2009/091856 and WO2014/200786, Mangion et al., 2011, *Org. Lett.* 13:5480-5483 and Miller et al., 2014, *Org. Lett.* 16:174-177.

The compound of Formula II and a mild silylating reagent are subjected to standard hydrogenation conditions. As the hydrogenation proceeds, silyl transfer takes place, resulting in the formation of silyl-protected hydroxylurea of formula III.

The reaction is conducted with an appropriate silylating agent. The silylating agent can be any agent that provides in situ protection of the hydroxyurea formed. The silylating agent can be selected from N,O-bis(trimethylsilyl)acetamide (BSA) or N,O-bis(trimethylsilyl)trifluoroacetamide (BSTFA). The silylating agent is typically present at slightly over 1 eq. In one embodiment, the silylating agent is N,O-bis(trimethylsilyl)acetamide present at 1.25 eq.

A catalyst system is used having one or more catalysts and optionally one or more catalyst activators. Suitable catalysts include palladium on carbon (Pd/C) or platinum on carbon (Pt/C), platinum (IV) oxide (PtO$_2$) and related catalysts such as Pd(OH)$_2$/C and Pd/Al$_2$O$_3$. The catalyst can be present at 4-100% (w/w).

In the absence of an amine base additive, an exemplary hydrogenation reaction required about 18 hr to complete with 18 wt % Pd/C catalyst (50% wet, 5% active Pd) and a number of impurities were observed. The presence of these impurities resulted in significantly lower yield and a less pure product which greatly impacts subsequent steps.

Addition of catalytic amounts of catalyst activators, e.g., certain amine bases, such as DABCO or triethylamine provided improvements on both the reaction rate and impurity suppression. For example, when 1 mol % DABCO was added to an exemplary reaction, complete conversion was obtained in 4 hours with less than half the amount of catalyst (8 wt %) and an a reaction mixture without structure related impurity. Suitable catalyst activators include DABCO and tertiary amines such as TEA, trimethylamine, N,N-Diisopropylethylamine (Hünig's base), triisopropylamine, and triphenylamine. The catalyst activator can be present at greater than 0.1 mol %, for example, at 0.5 mol %. In certain embodiments, the catalyst system comprises, or consists of, a combination of Pd/C and DABCO. In one embodiment, the Pd/C is present at 5% and the DABCO reagent is present at 1 mol %.

The reaction step is conducted in any non-nucleophilic solvent or mixtures thereof. Suitable solvents include DMF, acetonitrile, dichloromethane, THF, 2-MeTHF, EtOAc, IPAc, DMAc, toluene, NMP, DMPU, etc. The solvent or solvent mixture is present at between 8× to 30×. In the design of the reactions, it is advantageous to select a solvent or solvent mixture that can provide good solubility for the intermediate of Formula III, but poor solubility for a compound of Formula I. Suitable solvents and solvent mixtures include acetate solvents, including IPAc, EtOAc, MeOAc, methyl t-butyether, and toluene. In certain embodiments, the solvent is IPAc present at, for example, 10×.

The reaction can suitably be conducted at a temperature in a range of from about 10° C. to about 40° C. over the course of 1 to 24 hours. The hydrogen pressure is typically maintained in a range for 10-500 psi. In certain embodiments, the hydrogen pressure is about 50 psi.

This silyl protected intermediate of Formula III is very stable the reaction mixture or in the solution after the catalyst is removed by filtration. This is in stark contrast to prior methods in which a compound for Formula I was unstable in the solvent and continues to degrade during filtration. Moreover this intermediate improves solubility permitting the use of solvents other than THF during reaction and processing.

The isolation of the desired hydroxylurea product of Formula I from the silylated intermediate is achieved by a reactive direct crystallization (hydrolyzing) step. The direct crystallization step can be conducted in any non-nucleophilic solvent or mixture of solvents in which a compound of Formula I is insoluble. Suitable solvents include, MTBE, toluene, ether, an acid, EtOAc, and IPAc. Suitable acids include inorganic acids and organic acids, such as acetic acid. Water (or a mild nucleophile) can be included as a reagent. As discussed above, isopropyl acetate is favored as it can be used as a single solvent for the reaction and product isolation as well.

If THF is used as the solvent for the reaction, it is necessary to perform a solvent switch before hydrolyzing the compound of Formula III, to a solvent in which Formula I has low solubility.

The direct crystallization step may optionally be conducted in the presence of a weak acid suitable for removing a silyl as a protecting group. Suitable acids include, but are not limited to, acetic acid, carbonic acid, TsOH, MsOH, HBF$_4$, HCl, TFA, and H$_2$SO$_4$. In one embodiment, the acid is acetic acid. The acid is typically employed at 0.1-10 equivalents.

In one exemplary embodiment, after complete reaction and catalyst removal by filtration, the silyl protected hydroxyurea of formula III was added to 0.3 eq of acetic acid and 2.6 eq of water in IPAc.

The direct crystallization step can suitably be conducted at a temperature in a range of from about 10° C. to about 40° C. over the course of 1 to 24 hours and is typically conducted at a temperature in a range of from about 15° C. to about 20° C. over the course of 2 to 5 hours. In one exemplary embodiment, the direct crystallization step is conducted at a temperature of 15° C. for 3 hours.

Hydrolysis of the compound of Formula III resulted in precipitation of the less soluble hydroxylurea of Formula I in high yield and purity under very mild conditions for TMS removal.

The compound of Formula I may be further processed to obtain relebactam or a related compound through multiple means including but not limited to those described in International Patent Application Publication Nos. WO2009/091856 and WO2014/200786, Mangion et al., 2011, *Org. Lett.* 13:5480-5483 and Miller et al., 2014, *Org. Lett.* 16:174-177. The intermediate hydroxyurea 1 is a useful precursor to relebactam. Compound 1 can subsequently be processed as described in International Patent Application No. WO2010/126820 to obtain a beta lactamase inhibitor to prepare 7-oxo-1,6-diazabicyclo[3.2.1]octane-2-carboxamides and esters, in particular, the beta lactamase inhibitor, (2S,5R)-7-oxo-N-piperidin-4-yl-6-(sulfoxy)-1,6-diazabicyclo[3.2.1]octane-2-carboxamide.

Accordingly, in one aspect, the present invention provides a process for preparing compound 1:

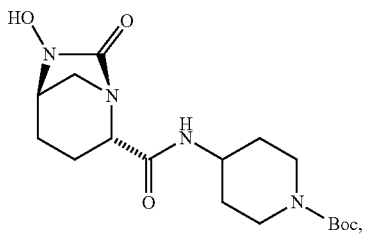

(1)

comprising (E1) reacting compound 2:

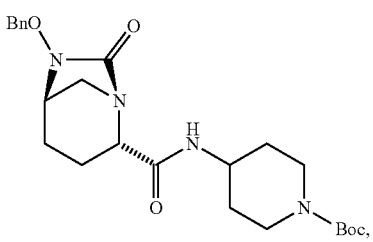

(2)

with a catalyst system and a silylating agent under hydrogenation conditions to obtain compound 3;

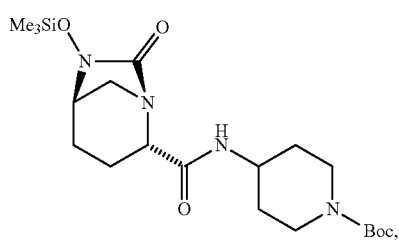

(3)

using the reagents and under the reactions conditions described above.

Exemplary Schemes

Scheme 1 - Reaction for preparing the hydroxylurea 1

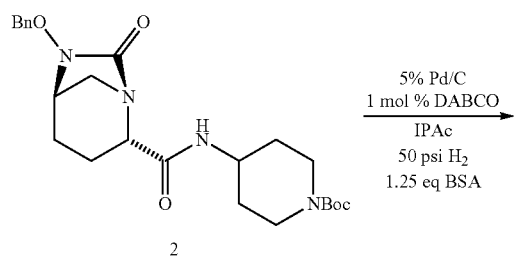

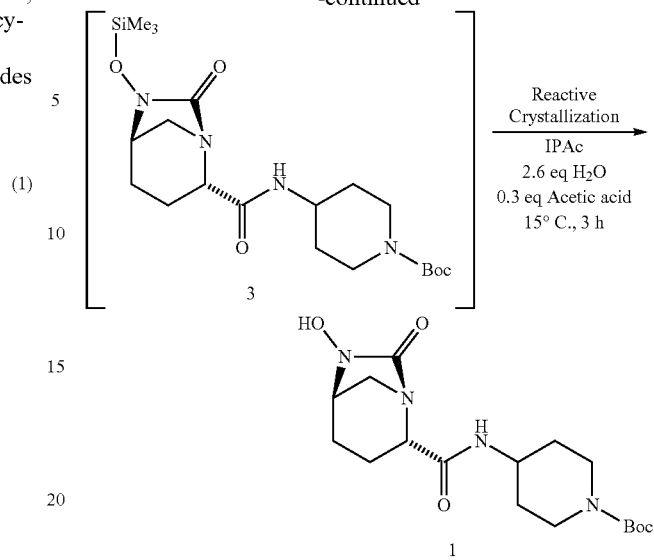

It is to be understood that the solvents, agents, catalysts, reaction amounts, reaction temperatures, etc. described above, its embodiments and aspects, and individual steps thereof, are intended only to illustrate, not limit, the scope of the process. For example, the solvent employed unless stated otherwise can be any organic substance which under the reaction conditions employed in the step of interest is in the liquid phase, is chemically inert, and will dissolve, suspend, and/or disperse the reactants and any reagents so as to bring the reactants and reagents into contact and to permit the reaction to proceed. Similar considerations apply to the choice of bases, catalysts, and other reagents employed in the process steps. Furthermore, each of the steps unless stated otherwise can be conducted at any temperature at which the reaction forming the desired product can detectably proceed. The reactants, catalysts and reagents in a given step can be employed in any amounts which result in the formation of at least some of the desired product. Of course, a high conversion (e.g., at least about 60% and preferably higher) of starting materials in combination with a high yield (e.g., at least about 50% and preferably higher) of desired products is typically the objective in each step, and the choice of solvents, agents, catalysts, reaction amounts, temperatures, etc. that can provide relatively good conversions and yields of product are preferred, and the choices that can provide optimal conversions and yields are more preferred. The particular solvents, agents, catalysts, reaction amounts, reaction temperatures, etc. described above, its embodiments and aspects, and the individual steps thereof can provide good to optimum conversions and yields.

The reaction times for the process steps described above depend upon such factors as (i) the choice and relative proportions of the starting substrate and other reagents, (ii) the choice of solvent, (iii) the choice of reaction temperature, and (iv) the level of conversion desired. The reactions are typically conducted for a time sufficient to achieve 100% or near 100% conversion (e.g., 99.5%, 99.0%, 98.0%, 97.0% or 95.0%).

The progress of any reaction step set forth herein can be followed by monitoring the disappearance of a reactant and/or the appearance of the desired product using such analytical techniques as TLC, HPLC, IR, NMR or GC.

Unless expressly stated to the contrary, all ranges cited herein are inclusive; i.e., the range includes the values for the upper and lower limits of the range as well as all values in between. For example, a phenyl ring described as optionally substituted with "1 to 3 substituents" is intended to include as aspects thereof, a ring substituted with 1 to 3 substituents, 2 to 3 substituents, 3 substituents, 1 to 2 substituents, 2 substituents, and 1 substituent. As another example, temperature ranges, ranges of equivalents, and the like described herein include the upper and lower limits of the range and any value in the continuum there between.

The present invention further relates to compounds including:

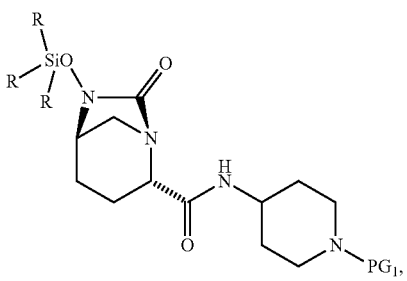

and salts thereof, wherein each R group is independently a $C_{1-6}$alkyl or phenyl, and $PG_1$ is an amine protecting group which forms with the amino nitrogen to which it is attached a carbamate, a benzylamine, or a sulfonamide. In certain embodiments, R is methyl. In certain embodiments, $PG_1$ is Boc. In one embodiment, the compound is

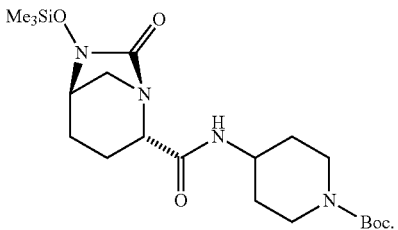

Abbreviations employed herein include the following:

| | |
|---|---|
| Ac | acetyl |
| Alloc | allyloxycarbonyl |
| BLI | beta-lactamase inhibitor |
| Bn | benzyl |
| Boc | t-butyloxycarbonyl |
| BSA | bis(trimethylsilyl)acetamide |
| BSTFA | N,O-bis(trimethylsilyl)trifluoroacetamide |
| Bz | benzoyl |
| Cbz | carbobenzoxy (alternatively, benzyloxycarbonyl) |
| DABCO | 1,4-diazabicyclo[2.2.2]octane |
| DIEA or DIPEA | N,N-diisopropylethylamine |
| DMAC or DMAc | N,N-dimethylacetamide |
| DMF | N,N-dimethylformamide |
| DMPU | 1,3-dimethyl-3,4,5,6-tetrahydro-2(1H)-pyrimidinone |
| DMT | dimethoxytrityl |
| EE | ethoxyethyl ethers |
| EtOAc | ethyl acetate |
| GC | gas chromatography |
| HPLC | high-performance liquid chromatography |
| HRMS | high resolution mass spectrometry |
| IPAc | isopropyl acetate |
| IR | infrared |
| KF | Karl Fischer |
| LCAP | Liquid Chromatography Area Percentage |
| MEM | β-methoxyethoxymethyl ether |
| MMT | methoxytrityl |
| MOM | methoxymethyl ether |
| Ms | methanesulphonyl |
| NMP | N-methyl pyrrolidinone |
| NMR | nuclear magnetic resonance |
| Pd/C | palladium on carbon |
| PG | protective (protecting) group |
| Piv | pivaloyl |
| PMB | p-methoxybenzyl ether |
| TBDMS | tert-butyldimethylsilyl |
| TBS | tert-Butyldimethylsilyl |
| Tf | trifluoromethanesulfonyl |
| TEA | triethylamine |
| TFA | trifluoroacetic acid |
| THF | tetrahydrofuran |
| THP | tetrahydropyranyl |
| TIPS | triisopropylsilyl |
| TLC | thin layer chromatography |
| TMS | trimethylsilyl |
| TOM | tri-isopropylsilyloxymethyl |
| Tr | trityl |
| TRIS | tris(hydroxymethyl)aminomethane |
| Ts | p-toluenesulphonyl |

The illustrative examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents allowed under the definitions of Formula I defined above.

The processes of the instant invention are useful in the preparation of compounds of Formula I. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice. The examples are not to be construed as limitations on the scope or spirit of the invention.

EXAMPLES

Example 1

Preparation of TMS-Hydroxylurea Intermediate

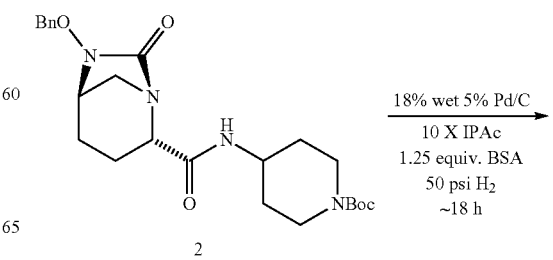

2

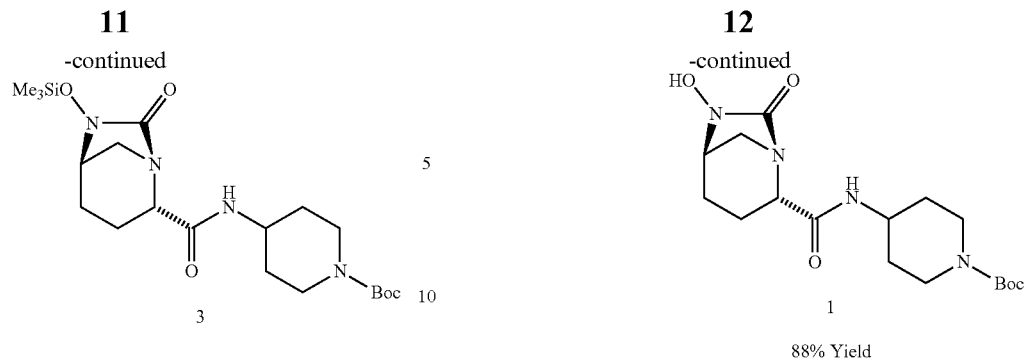

To a 2 L three neck round bottom flask containing 18.0 g of 5% Pd/C (50% water) was added 1.2 L isopropyl acetate. The mixture was distilled at one atmosphere and about 600 ml was collected until the KF moisture content of the remaining mixture was <500 ppm. The mixture was cooled to room temperature and another 400 ml of isopropyl acetate was added, followed by 100.0 g (0.22 mol) of compound 2 and 68.0 ml (95%, 1.25 eq) of N,O-bis(trimethylsilyl)acetamide (free of trace of triethylmine). The mixture was then hydrogenated in an autoclave at 50 psi and room temperature for about 18 hours until the remaining starting material was less than 0.5% as assessed by HPLC analysis. The mixture was filtered through Celite® (filter agent from diatomaceous earth) and the cake was rinsed with 500 ml isopropyl acetate. The HPLC analysis of the reaction mixture indicated that the yield of desired product 3 was 95% with several impurities, including impurities that resulted from removal of Boc protecting group and cleavage of N—O bond as two of the major impurities.

Example 2

Preparation of Hydroxylurea Intermediate with Catalyst Activator

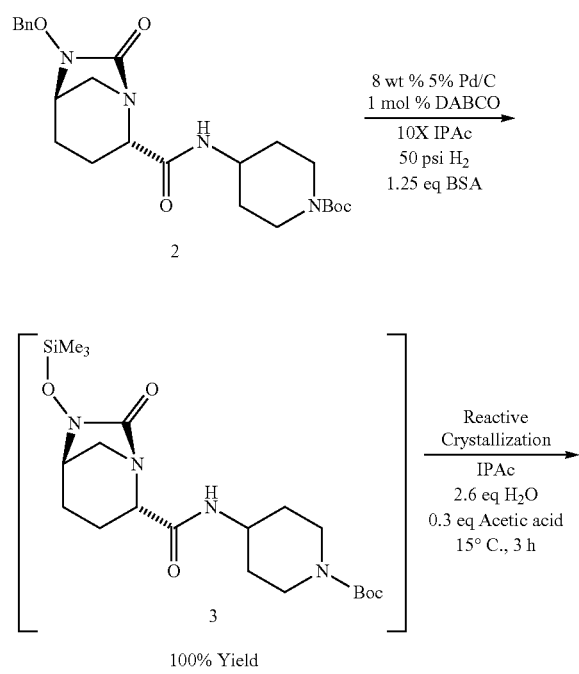

Part A: Hydrogenation

To a 2 L three neck round bottom flask containing 8.0 g of 5% Pd/C (50% water) was added 1.0 L isopropyl acetate. The mixture was distilled at one atmosphere and about 300 ml was collected until the KF moisture content of the remaining mixture was <500 ppm. The mixture was cooled to room temperature and another 400 ml of isopropyl acetate was added, followed by 100.0 g (0.22 mol) of compound 2, 68.0 ml (95%, 1.25 eq) of N,O-bis(trimethylsilyl)acetamide and 0.24 g (1 mol %) of DABCO. The mixture was then hydrogenated in an autoclave at 50 psi and room temperature for about 5 hours until the remaining starting material was less than 0.5% as assessed by HPLC analysis. The mixture was filtered through Celite® (Filter agent from diatomaceous earth) and the cake was rinsed with 500 ml isopropyl acetate. HPLC analysis indicated that the yield of intermediate 3 in solution was 100% without structurally-related impurities. The solution was then concentrated at reduced pressure until the batch volume was 1.4 L. The solution was used directly for reactive crystallization in Part B.

Analytical pure crystalline 3 was isolated by concentrating the batch solution to 800 ml and allowing the solution to age overnight at room temperature. $^1$H NMR (CDCl$_3$) δ 6.64 (d, 1H), 4.10-3.97 (br, 2H), 3.90-3.96 (m, 2H), 3.58 (s, 1H), 3.17 (d, 1H), 2.87 (t, 2H), 2.78 (d, 1H), 2.37 (m, 1H), 2.12 (m, 1H), 2.05-1.97 (m, 1H), 1.80 (t, 2H), 1.70 (m, 1H), 1.46 (s, 9H), 1.32 (m, 2H), 0.27 (s, 9H). $^{13}$CNMR (CDCl$_3$) δ 169.05, 168.16, 154.67, 79.70, 60.54, 59.84, 47.16, 46.75, 32.02, 31.76, 28.39, 20.31, 17.40, 1.91, 1.33, −0.88. (+)-ESI HRMS: C$_{20}$H$_{36}$N$_4$NaO$_3$Si, (M+Na)$^+$463.2347, found 463.2348.

Part B: Reactive Crystallization

To a three neck round bottom flask was added 400 ml of the batch solution from Part A. The solution was cooled to 15° C. and 5.5 g acetic acid aqueous solution (28 wt % acetic acid) was added in one portion followed by 1.0 g product seeds. The mixture was then agitated at 15° C. for one hour while adding one third of the remaining batch solution slowly. To the resulting suspension was added another 4.17 g of acetic acid aqueous solution in one portion. The mixture was agitated while another one third of batch solution was added slowly over one hour. After adding another 4.17 g of acetic acid aqueous solution, the rest of the batch solution was added over one hour. The resulting suspension was agitated at 20° C. for one hour followed by addition of 600 ml of methyl tert-butylether. The mixture was then cooled to 5° C. over one hour and the product was collected by filtration. The cake was washed with 200 ml of isopropyl acetate. The cake was dried in a vacuum oven at 50° C., to give 70.7 g (88%) of 1 as a colorless solid.

Comparing the experimental results from Example 1 and 2, the addition of DABCO to the hydrogenation mixture not only accelerated the reaction rate, which led to less catalyst required, but also eliminated the formation of undesired side reactions and improved the product yield and purity.

Example 3

Preparation of Hydroxylurea Using TBAF and Water for Deprotection

Compound 2 (10.0 g, 22 mmol) was subjected to hydrogenation under the same conditions as described in EXAMPLE 2. The resulting TMS-protected hydroxylurea intermediate solution in isopropyl acetate was then cooled to 15° C. Tetrabutylammonium fluoride trihydrate (0.16 g, 2.4 mol %) was then added followed by 0.5 g (1.29 equiv.) of water. The mixture was stirred for an additional 2 hours to give a suspension. Methyl t-butylether (50 ml) was then added and the suspension was cooled to 5° C. The mixture was filtered and washed and dried similarly as described in EXAMPLE 2, to give 6.8 g (85%) compound 1.

While the foregoing specification teaches the principles of the present invention, with examples provided for the purpose of illustration, the practice of the invention encompasses all of the usual variations, adaptations and/or modifications that come within the scope of the following claims.

What is claimed:

1. A process for preparing a compound of Formula I, or a salt thereof:

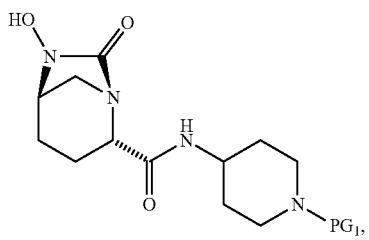

(I)

comprising
(A) reacting a compound of Formula II:

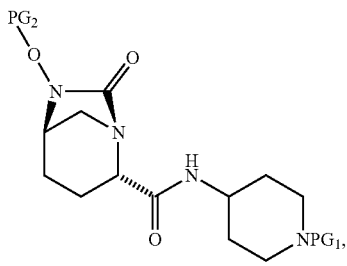

(II)

with a catalyst system and silylating agent under hydrogenation conditions to obtain a compound of Formula III;

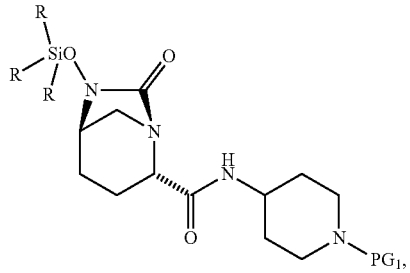

(III)

wherein each R group is independently a $C_{1-6}$ alkyl or phenyl; and
(B) hydrolyzing the compound of Formula III to form the compound of Formula I, wherein $PG_1$ is an amine protecting group which forms with the amino nitrogen to which it is attached a carbamate, a benzylamine, or a sulfonamide; and $PG_2$ is an oxygen protecting group selected from benzyl (Bn), substituted benzyl, trityl, and substituted trityl.

2. The process according to claim 1, wherein the silylating agent is selected from N,O-bis(trimethylsilyl)acetamide (BSA) or N,O-bis(trimethylsilyl)trifluoroacetamide (BSTFA).

3. The process according to claim 2, wherein the silylating agent is N,O-bis(trimethyl silyl)acetamide (BSA).

4. The process according to claim 1, wherein the catalyst system comprises Pd/C palladium on carbon (Pd/C), platinum on carbon (Pt/C), platinum (IV) oxide ($PtO_2$), PdOH/C, or $Pd/Al_2O_3$.

5. The process according to claim 4, wherein the catalyst system further comprises a catalyst activator selected from DABCO and TEA.

6. The process according to claim 1, wherein the catalyst system comprises Pd/C at 4-100% (w/w) and DABCO from 0.1 mol % to 100 mol %.

7. The process according to claim 1, wherein Step A is conducted in a solvent selected from DMF, acetonitrile, dichloromethane, THF, 2-MeTHF, EtOAc, IPAc, DMAc, toluene, NMP, and DMPU.

8. The process according to claim 7, wherein the solvent is IPAc.

9. The process according to claim 1, wherein Step B is conducted in a solvent selected from MTBE, toluene, ether, an acid, EtOAc, and IPAc, wherein the solvent is mixed with water as a reagent.

10. The process according to claim 1, wherein Step B occurs in the same solvent as in Step A.

11. The process according to claim 10, wherein the solvent is IPAc.

12. The process according to claim 1, wherein $PG_1$ is Boc and $PG_2$ is benzyl.

13. A compound of Formula III:
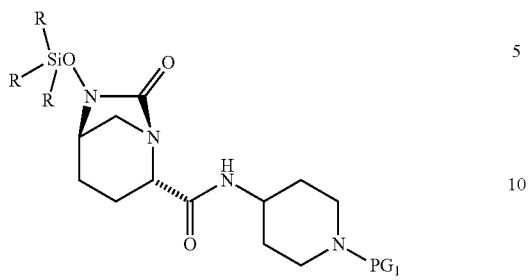
or a salt thereof, wherein each R group is independently a $C_{1-6}$ alkyl or phenyl; and
$PG_1$ is an amine protecting group which forms with the amino nitrogen to which it is attached a carbamate, a benzylamine, or a sulfonamide.
14. The compound of claim 13, wherein each R is methyl and $PG_1$ is Boc.
* * * * *